United States Patent [19]

Wildfeuer

[11] Patent Number: 5,521,294
[45] Date of Patent: May 28, 1996

[54] 2,2-DIFLUORO-3-CARBAMOYL RIBOSE SULFONATE COMPOUNDS AND PROCESS FOR THE PREPARATION OF BETA NUCLEOSIDES

[75] Inventor: Marvin E. Wildfeuer, Lafayette, Ind.

[73] Assignee: Eli Lilly and Company, Indianapolis, Ind.

[21] Appl. No.: 373,998

[22] Filed: Jan. 18, 1995

[51] Int. Cl.$^6$ ............................. C07H 5/04; C07H 5/06; C07H 19/073
[52] U.S. Cl. .................... 536/18.7; 536/27.11; 536/28.5; 536/28.51; 514/29
[58] Field of Search ............................. 536/18.2, 27.11, 536/28.5, 28.51

[56] References Cited

U.S. PATENT DOCUMENTS

| | | | |
|---|---|---|---|
| 2,949,449 | 8/1960 | Hoffer | 536/28.54 |
| 3,575,959 | 4/1971 | Shen et al. | 536/27.6 |
| 3,658,786 | 4/1972 | Albrecht et al. | 536/27.23 |
| 4,526,988 | 7/1985 | Hertel | 549/313 |
| 4,656,260 | 4/1987 | Kato et al. | 536/55 |
| 4,760,137 | 7/1988 | Robins et al. | 536/27.11 |
| 4,808,614 | 2/1989 | Hertel | 514/45 |
| 4,904,771 | 2/1990 | Katsunuma et al. | 536/66 |
| 4,954,623 | 9/1990 | Nagarajan | 536/127 |
| 4,965,374 | 10/1990 | Chou et al. | 549/313 |
| 5,070,190 | 12/1991 | Lockhoff et al. | 536/29.1 |
| 5,216,145 | 6/1993 | Raifeld | 536/111 |
| 5,371,210 | 12/1994 | Chou | 536/27.11 |
| 5,424,416 | 6/1995 | Jones | 536/27.11 |

OTHER PUBLICATIONS

Okauchi et al., "Stereoselective Synthesis of β–2–Deoxyribonucleosides from 1–O–Acetyl–3–O–[2–(methylsulfinyl)ethyl]–2–ribose," *Chemistry Letters*, 1989, 801–804.

Ichikawa et al., "Stereoselective β–C– and β–S–Glycosylation of 2–Deoxyribofuranose Derivatives Controlled by the 3–Hydroxy Protective Group," *Bull. Chem. Soc. Japan*, 62(3), 845–852 (1989).

Wierenga et al., "Stereochemical Control as a Function of Protecting–Group Participation in 2–Deoxy–D–erythro–pentofuranosyl Nucleosides," *Carbohydrate Res.*, 90, 41–52 (1981).

Plusquellec et al., "Sugar Chemistry Without Protecting Groups: A Regioselective Addition of the Primary Hydroxyl of Monosaccharides to Alkylisocyanates," *Tetrahedron Letters*, 28(36), 4165–4168 (1987).

Wolfrom et al., "Crystalline Phenylurethans (Carbanilates) of Sugar Glycosides", *J. Am. Chem. Soc.*, 62, 1151–1153 (1940).

C. B. Reese, "Protection of Alcoholic Hydroxyl Groups and Glycol Systems," Ch. 3 in *Protective Groups in Organic Chemistry*, Plenum Press, New York, NY, 1973, pp. 95–143.

Goodman (I), "Chemical Syntheses and Transformations of Nucleosides. Synthesis of Nucleosides," Ch. 2, Sect. II in *Basic Principles in Nucleic Acid Chemistry*, vol. 1, Ts'O et al. (eds.), Academic Press, New York, NY, 1974, pp. 95–128, particularly pp. 104–105.

Goodman (II), "Chemical Syntheses and Transformations of Nucleosides. Chemical Transformations That Involve both the Sugar and the Heterocyclic Base; Pyrimidine Cyclonucleosides," Ch. 2, Sect. V, Part 2 in *Basic Principles in Nucleic Acid Chemistry*, vol. 1, Ts'O et al. (eds.), Academic Press, New York, NY, 1974, pp. 177–190.

Protective Groups in Organic Synthesis, Greene, John Wiley & Sons, N.Y., Chapter 2 (1981), pp. 10–86.

*Primary Examiner*—Douglas W. Robinson
*Assistant Examiner*—L. Eric Crane
*Attorney, Agent, or Firm*—Margaret M. Brumm; Robert A. Conrad; David E. Boone

[57] ABSTRACT

This invention provides novel 1-alkylsulfonyl-2,2-difluoro-3-carbamoyl ribose intermediates and intermediate nucleosides derived therefrom. The compounds are particularly useful in the preparation of 2'-deoxy-2',2'-difluoro-beta-cytidine and other beta anomer nucleosides which are antiviral and anticancer agents.

21 Claims, No Drawings

2,2-DIFLUORO-3-CARBAMOYL RIBOSE SULFONATE COMPOUNDS AND PROCESS FOR THE PREPARATION OF BETA NUCLEOSIDES

BACKGROUND OF THE INVENTION

The present invention relates to novel 1-alkylsulfonyl-2, 2-difluoro-3-carbamoyl-5-protected ribose derivatives and to a process using such compounds to prepare intermediate nucleobases to antiviral alpha and beta nucleosides. In particular the present invention relates to novel nucleobases which are intermediates to 2'-deoxy-2',2'-difluoro-beta-cytidine, an antiviral agent and anticancer agent.

The prior art synthesis of 2'-deoxy-2',2'-difluoro-beta-cytidine involves reaction of silylated cytosine with a dibenzylated ribose mesylate intermediate according to the following reaction (Equation 1):

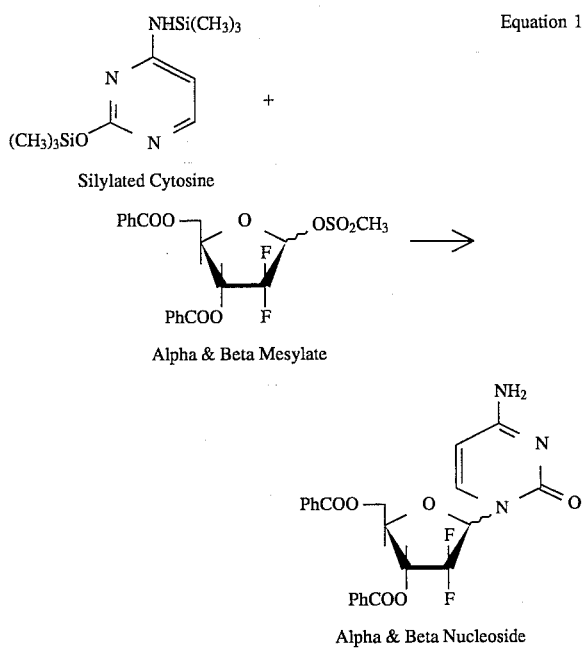

Under conditions where substitution of the mesylate by cytosine is preceded by elimination of mesylate to give a charged intermediate (SN1), a mixture of alpha and beta anomers (the beta anomer is desired) is obtained. The alpha and beta nucleosides are deprotected in a conventional manner and then separated.

In classical methods of nucleoside synthesis, where there is an acylated hydroxy group on the neighboring 2-carbon of the ribose, the participation of the acyl group in the substitution reaction favors formation of the beta isomer (Goodman, L., Basic Principles in Nucleic Acid Chemistry, Volume 1, pp. 94–208, Academic Press, New York (1974)) as shown by the following reaction (Equation 2):

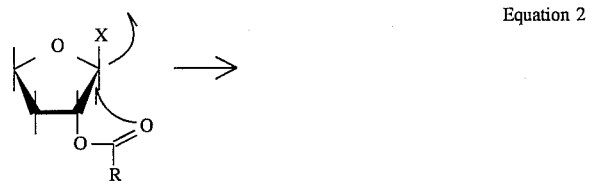

Since the dibenzylated ribose mesylate intermediate in 2'-deoxy-2', 2'-difluoro-beta-cytidine synthesis of 2'-deoxy-2', 2'-difluoro-beta-cytidine contains no 2-hydroxy group, such participation cannot occur.

In principle, substituents on either the 3- or 5-hydroxyls of ribose could be used to direct facial selectivity in such reactions. The 2-(methylsulfinyl)ethyl group has recently been recommended as a 3-OH protecting group which imparts good β-selectivity in glycosylation reactions with 2-deoxyribose derivatives. Unfortunately, convenient methods for the introduction of this group are not currently available. See: Okauchi, T.; Kubota, H.; Narasaka, K., Chem. Lett. 801–804 (1989), and Ichikawa, Y.; Kubota, H.; Fujita, K.; Okauchi, T.; Narasaka, K., Bull. Chem. Soc. Japan, 62, 845–852 (1989); Wierenga, W.; Skulnick, H. I., Carbohydr. Res., 90, 41–52 (1981). In practice, relatively low levels of stereocontrol have generally been achieved by this strategy and the factors responsible are not always clear. Although bicyclic cations of type A and B below have been proposed as intermediates in such glycosylation reactions (Wierenga, W., et al., Carbohydr. Res., 90, 41–52 (1981)) their significance in influencing product ratios is a debatable point.

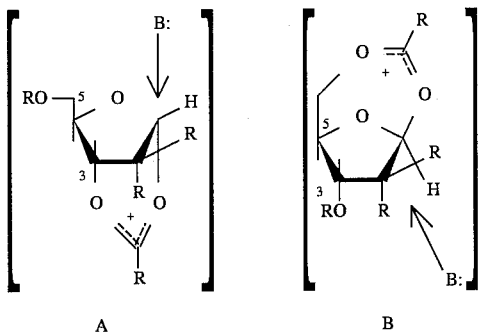

In situations where both the 3- and 5-hydroxyls are acylated, competition of both types of bicyclic cation for the nucleophile could result in a low level of stereoselection since they lead to products of opposite configuration.

The concept of using the substituent on the 3 hydroxy of deoxyribofuranose derivatives to direct beta synthesis is described by Ichikawa et al (Ichikawa, Y., et al., Bull. Chem. Soc. Japan, 62(3), 845–852 (1989)). They used a methylthioethyl substituent or especially its corresponding sulfoxide at the 3 position of a 2-deoxyribose sugar to successfully enhance beta substitution of silylated nucleophiles to form C-glycosides. Similarly, they formed predominantly beta S-glycosides when reacting the 2-deoxyribose sugar containing a 2-pyridylmethyl N-oxide protective group at the 3 position with trimethylsilyl sulfides. There was no disclosure of the use of nucleobases Although both aryl and alkyl carbamates have been used for selective protection of sugar hydroxyls (Plusquellec, D., et al., Tetrahedron Let., 28, 4165–4168 (1987)) or to obtain crystalline sugar derivatives (Wolfrom, M. L., et al., J. Am. Chem. Soc., 62, 1151–1153 (1940)), no use is reported in the literature for the purpose of directing nucleobase addition to the beta anomeric carbon (C1) position in forming a nucleoside.

It is therefore an object of the present invention to provide novel intermediates which produce a high percentage yield of the beta anomer nucleoside, compared to the alpha anomer when used in the preparation of intermediates to 2'-deoxy-2',2'-difluoro-beta-cytidine and analogous compounds. Further, it is an object of the present invention to provide novel beta anomer nucleosides from the intermediate compounds. Further still, it is an object to provide a process for producing the compounds which is relatively economical and which particularly can be used in producing 2'-deoxy-2',2'-difluoro-beta-cytidine and other beta anomer nucleosides in bulk. These and other objects will become increasingly apparent by reference to the following description.

SUMMARY OF THE INVENTION

The present invention relates to sulfonate intermediates of the formula

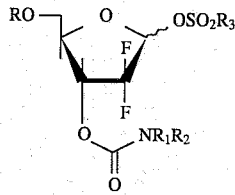

wherein R is a hydroxy protecting group, $R_1$ and $R_2$ are each selected from the group consisting of hydrogen, unsubstituted and substituted $C_1$–$C_8$ alkyl, and unsubstituted and substituted phenyl, and $R_3$ is $C_1$–$C_8$ alkyl.

The present invention also relates to a process for the preparation of a beta nucleoside of the formula:

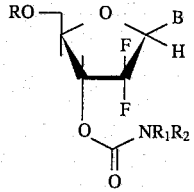

where B is a protected pyrimidine nucleobase residue as set forth in detail hereinafter, which comprises:

reacting a sulfonate intermediate of the formula:

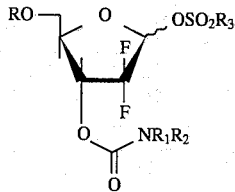

with a protected pyrimidine nucleobase B-H in the presence of a Lewis acid in a non-reactive solvent at a temperature between about 80° and 120° C, wherein R is a hydroxy protecting group, $R_1$ and $R_2$ are each selected from the group consisting of hydrogen, unsubstituted and substituted $C_1$–$C_8$ alkyl, and unsubstituted and substituted phenyl, and $R_3$ is $C_1$–$C_8$ alkyl. The invention also relates to the additional step of deprotecting the beta nucleoside using conventional deprotecting means well known to those skilled in the art.

The present invention also relates to lactone intermediates of the formula:

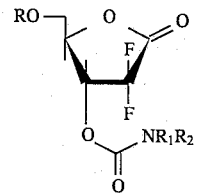

wherein R is a hydroxy protecting group, $R_1$ and $R_2$ are each selected from the group consisting of hydrogen, unsubstituted and substituted $C_1$–$C_8$ alkyl, and unsubstituted and substituted phenyl.

The present invention further relates to lactol intermediates of the formula:

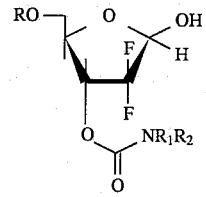

wherein R is a hydroxy protecting group, $R_1$ and $R_2$ are each selected from the group consisting of hydrogen, unsubstituted and substituted $C_1$–$C_8$ alkyl, and unsubstituted and substituted phenyl.

Finally, the present invention also relates to nucleoside intermediates of the formula

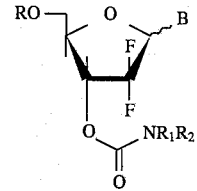

wherein R is a hydroxy protecting group, $R_1$ and $R_2$ are each selected from the group consisting of hydrogen, unsubstituted and substituted $C_1$–$C_8$ alkyl, and unsubstituted and substituted phenyl, and B is selected from the group consisting of a protected and unprotected pyrimidine nucleobase residue.

DETAILED DESCRIPTION AND PREFERRED EMBODIMENTS

The following definitions refer to the various terms used throughout this disclosure. The term "halo" refers to fluoro, chloro, bromo, and iodo. The term "$C_1$–$C_8$ alkyl" refers to the straight and branched aliphatic radicals of 1 to 8 carbon atoms such as methyl, ethyl, propyl, isopropyl, n-butyl, sec-butyl, tert-butyl, n-pentyl, 2,2-dimethylpropyl, hexyl, octyl, and the like. The term "substituted $C_1$–$C_8$ alkyl" refers to $C_1$–$C_8$ alkyl which is substituted by one or more groups selected from hydroxy, halo, and ($C_1$–$C_8$ alkyl)—O—, such as trifluoromethyl, 2-methoxyethyl, 3-hydroxy-6-methylheptyl, and the like. The term "substituted phenyl" refers to a phenyl group which is substituted by one, two, or three groups selected from $C_1$–$C_8$ alkyl, hydroxy, halo, nitro, and ($C_1$–$C_8$ alkyl)—O—, such as 4-t-butoxyphenyl, 3,4-dichlorophenyl, 3,5-dihydroxy-4-t-butylphenyl, and the like.

It is recognized that the lactol, sulfonates, and nucleoside intermediates claimed in this invention may 5 exist in either the alpha or beta form. This invention is not limited to any particular isomer but includes both individual isomers and mixtures thereof.

The present discovery uses the 3-hydroxy carbamoyl group on the difluororibose intermediate to enhance formation of the desired beta anomer nucleoside derivative. The 3-carbamoyl group favors attack by the silylated cytosine (or other nucleobase "B—H") from the opposite side, thus favoring formation of the beta nucleoside derivative (Equation 3).

Equation 3

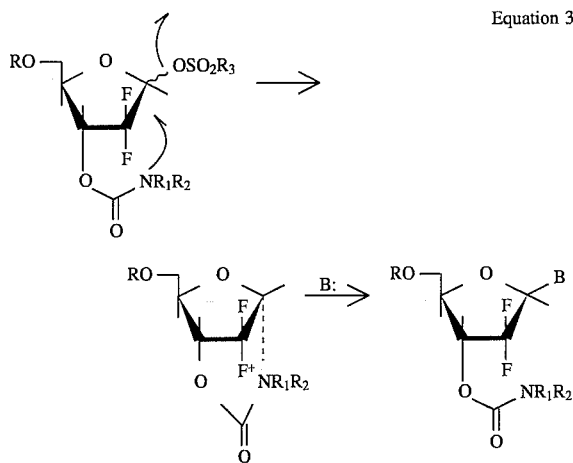

Isocyanates of the formula $R_1NCO$ can be used to prepare the 3-carbamoyl derivatives.

Phenyl isocyanate (R=phenyl) can be used. Analogous derivatives are produced from diphenyl carbamoyl chloride ($R_1$=$R_2$=phenyl), dimethyl carbamoyl chloride ($R_1$=$R_2$=methyl), nitrophenyl isocyanate ($R_1$=nitrophenyl) and the like. The phenyl or alkyl moieties can be substituted with various groups such as halogens, ethers, esters, alkyl and the like, so long as they are non-interfering.

The 3-carbamoyl intermediates of this invention are of a nature such that the hydroxy groups must be protected to keep them from reacting with the nucleobase, or being decomposed in some manner. The protecting groups for the 5-position are chosen from the groups used in synthetic organic chemistry for this purpose. Chemists are accustomed to choosing groups which can be efficiently placed on hydroxy groups, and which can be easily removed when the reaction is complete. Suitable groups are described in standard textbooks, such as Chapter 3, of Protective Groups in Organic Chemistry, McOmie, Ed., Plenum Press, New York (1972); and Chapter 2 of Protective Groups in Organic Synthesis, Greene, John Wiley & Sons, New York (1981).

For example, hydroxy-protecting groups include such as formyl, 2-chloroacetyl, benzyl, diphenylmethyl, benzoyl, triphenylmethyl, 4-nitrobenzyl, phenoxycarbonyl, t-butyl, methoxymethyl, tetrahydropyranyl, allyl, tetrahydrothienyl, 2-methoxyethoxymethyl, methoxyacetyl, phenoxyacetyl, isobutyryl, ethoxycarbonyl, benzyloxycarbonyl, and the like. Silyl hydroxy-protecting groups are often particularly convenient, because most of them are easily cleaved by contact with water or an alcohol. Such groups include especially trimethylsilyl, as well as isopropyldimethylsilyl, methyldiisopropylsilyl, triisopropylsilyl and the like. The t-butyldimethylsilyl group is a special case; it is more difficultly cleaved and requires a reagent such as a hydrohalic acid to remove it from the hydroxy groups. A carbamoyl group can be used in the 5-position which is the same as or different from the directing group in the 3-position.

The reactions to form the mesylate ($R_3$=$CH_3$) are conventional. A molar excess of an isocyanate or carbamoyl halide with the appropriate $R_1$ and $R_2$ groups is reacted with the hydroxy at the 3-position of the ribose on a 5-protected intermediate. The reaction is conducted in the presence of a catalytic or reaction promoting amount, preferably 0.1 to 2 equivalents, of an amine base and a non-reactive solvent for the reactants, preferably ethyl acetate. The amine can be triethylamine or DMAP. The reaction is generally conducted at temperatures between 20 and 80° C.

The pyrimidine nucleobase derivatives employed herein to form the B group of the nucleoside are commonly known to organic chemists and no discussion of their synthesis is necessary. However, in order to be useful in the present glycosylation process the nucleobase derivatives (B—H) or their tautomeric equivalents, bearing amino or hydroxy groups preferably contain primary amino protecting groups (W) and/or hydroxy protecting groups (Z), depending on the nature of the nucleobase derivative selected. The protecting group blocks the hydroxy or amino groups which may provide a competing reaction site for the carbohydrate. The protecting groups are attached to the nucleobase derivative before it is reacted with the 3-carbonyl protected ribose compounds of the present invention and are removed subsequent thereto. A procedure for protecting the nucleobase derivatives is described in U.S. Patent No. 4,526,988 to Hertel.

Preferred amino protecting groups (W) for pyrimidine nucleobase derivatives are selected from the group consisting of silyl ether forming groups such as trialkylsilyl, t-butyldialkylsilyl and t-butyldiarylsilyl; carbamates such as t-butoxycarbonyl, benzyloxycarbonyl, 4-methoxybenzyloxycarbonyl, and 4-nitrobenzyloxycarbonyl, formyl, acetyl and benzoyl; ether forming groups such as methoxymethyl, t-butyl, benzyl, allyl and tetrahydropyranyl; more preferred is trimethylsilyl. Preferred hydroxy protecting groups (z) for pyrimidine nucleobase derivatives are selected from silyl ether forming groups, trialkylsilyl carbamates such as t-butoxycarbonyl, benzyloxycarbonyl, 4-methoxybenzyloxycarbonyl and 4-nitrobenzyloxycarbonyl; carbocyclic esters such as formyl, acetyl, and pivalamido; preferred is trimethylsilyl.

Thus B—H is a nucleobase selected from the group consisting of

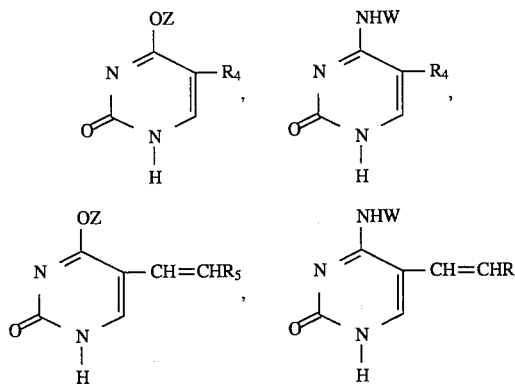

-continued

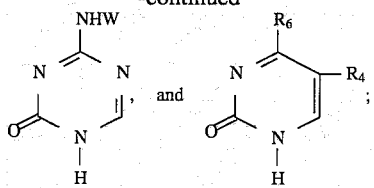

and the protected pyrimidine nucleobase residue B—is

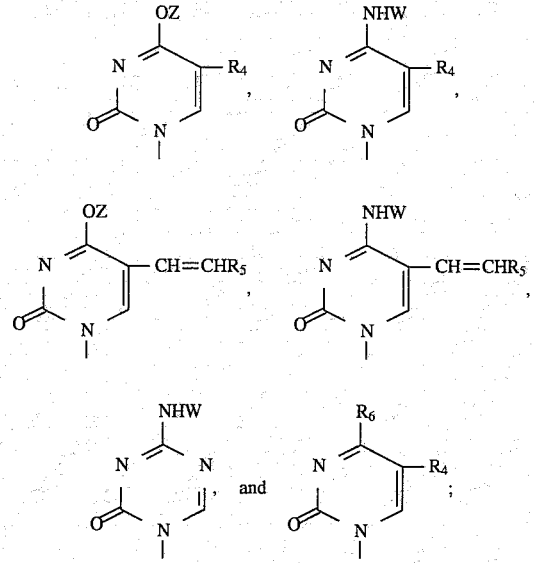

wherein $R_4$ is selected from the group consisting of hydrogen, unsubstituted and substituted $C_1$–$C_8$ alkyl, and halo; $R_5$ and $R_6$ are selected from the group consisting of hydrogen, unsubstituted and substituted $C_1$–$C_8$ alkyl, and halo; Z is a hydroxy protecting group and W is an amino protecting group. An unprotected pyrimidine nucleobase residue referred to herein is a B-moiety wherein each Z and/or W group is hydrogen, and tautomers thereof.

In providing protectible groups to the nucleobase derivatives the protecting group itself may be protected. For example, N-acetylcytosine may be protected with trimethylsilyl to form trimethylsilyl-N-acetylcytosine.

In addition, it is often advisable to convert any keto oxygen atoms on the nucleobase derivative to enol form. This makes the nucleobase derivative more aromatic and enhances the reactivity of the nucleobase derivative. It is most convenient to enolize the keto oxygens and provide silyl protecting groups for them. Thus, another form of nucleobase "B—H" which can be employed in this invention are the corresponding tautomers of the above in which the enol group is protected with a Z-moiety:

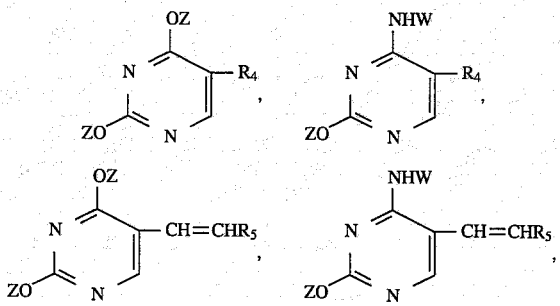

-continued

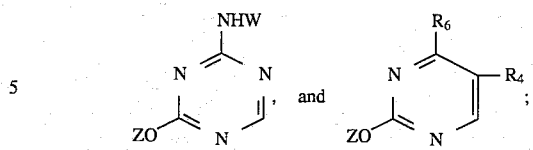

In a preferred embodiment of the present process the nucleobase derivative is of the formula

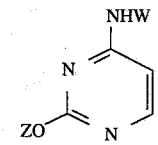

wherein Z and W are trimethylsilyl, otherwise referred to as trimethylsilyl protected cytosine.

The reaction solvents suitable for use in the present glycosylation process must be inert to the glycosylation reaction and have a freezing point temperature from about 40° C. to about –120° C. The preferred reaction solvent is xylene. Other solvents are p- or o-dichlorobenzene, trimethylsilyl phenoxide, tetraline and other non-polar solvents.

In accordance with the present process, at least an equimolar amount of nucleobase derivative should be employed relative to the amount of carbohydrate employed. However, it is more preferable to use a molar excess of nucleobase derivative. The reaction is conducted in the presence of a Lewis acid. The Lewis acid which provides the best results is trimethylsilyl triflate. Numerous other Lewis acids can be used such as:

Tin (II) Chloride
Tin (IV) Chloride
Titanium (IV) Chloride
$BF_3$ etherate
Triethylborane
TMSCl/KI
$BBr_3$
TMSI
$TMS_2SO_4$
p-TsOH
$BF_3$ $Et_2O$ (in AmOAc)
Ti (IV) isopropoxide
Al $Et_3$
Si(isopropyl)$_3$ triflate
TMS $O_2$ $CCF_3$
TBS triflate
Si(mt)$_3$ triflate
TMS mesylate
TMS benzenesulfonate
TMS phenoxide where TMS is a trimethylsilyl group and TBS is a tertiary butyldimethylsilyl group.

Although not critical, it is advisable that the reaction between the 3-carbamoyl ribose intermediates and the nucleobase derivative be carried out in a dry atmosphere, e.g. in dry air, nitrogen or argon. This is because certain nucleobase derivatives are moisture sensitive.

The progress of the present glycosylation process is followed by procedures well known to one of ordinary skill in the art such as high pressure liquid chromatography (HPLC) and thin layer chromatography (TLC) which can be used to detect the presence of nucleoside product.

In accordance with the present glycosylation process, the beta-anomer nucleosides are generally prepared in a beta anomer ratio of 50:50 to about 60:40 beta to alpha anomer.

The final phase of the reaction sequence is the removal of any 3- and/or 5-protecting groups R, Z and/or W from the blocked nucleoside. The same anomeric ratio of unprotected nucleoside is obtained by removal of the protecting groups.

Most silyl and silyl-amino protecting groups are easily cleaved by use of a protic solvent, such as water or an alcohol. The acyl protecting groups, such as benzoyl and the acyl-amino protecting groups, are removed by hydrolysis with a strong base at a temperature from about 0° C. to about 100° C. Strong or moderately strong bases suitable for use in this reaction are bases which have a pKa (at 25° C.) of about 8.5 to about 20.0. Such bases include alkali metal hydroxides such as sodium or potassium hydroxide; alkali metal alkoxides such as sodium methoxide or potassium t-butoxide; alkali metal amides; amines such as diethylamine, hydroxylamine, ammonia and the like; and other common bases such as hydrazine and the like. Although a catalytic amount of base may be used, in practice an excess is used to accelerate the reaction.

The acyl protecting groups can also be removed with acid catalysts, such as methanesulfonic acid, hydrochloric acid, hydrobromic acid, sulfuric acid, or with acidic ion exchange resins. It is preferred to carry out such hydrolysis at relatively high temperature, such as the reflux temperature of the mixture, but temperatures as low as ambient may be used when particularly strong acids are used.

The removal of ether protecting groups is carried out by known methods, for example, with ethanethiol and aluminum chloride.

The t-butyldimethylsilyl protecting group requires acidic conditions, such as contact with gaseous hydrogen halide, for its removal.

Removal of the protecting groups may be conveniently carried out in alcoholic solvents, especially aqueous alkanols such as methanol. However, the deblocking reaction may also be carried out in any convenient solvent, such as polyols including ethylene glycol, ethers such as tetrahydrofuran, ketones such as acetone and methyl ethyl ketone, or dimethylsulfoxide.

In a preferred embodiment, the deblocking reaction employs ammonia to remove a benzoyl hydroxy-protecting group at a temperature of about 10° C. It is preferable, however, to use an excess of base in this reaction, although the amount of excess base used is not crucial.

The resulting beta-anomer enriched nucleosides can be extracted and/or isolated from the reaction mixture by the techniques described in U.S. Pat. No. 4,965,374 to Chou, T. which is incorporated herein by reference.

EXAMPLE 1

Difluororibonic acid lactone was reacted with phenyl isocyanate. The resulting bis-3,5-phenylcarbamoyl lactone (I) was obtained as a crystalline derivative. Reduction with lithium aluminum hydride to form the 1-hydroxide (II) and reaction with methanesulfonyl chloride gave a mixture of alpha and beta-1-mesylates (III). The reactions are as follows (Equation 4):

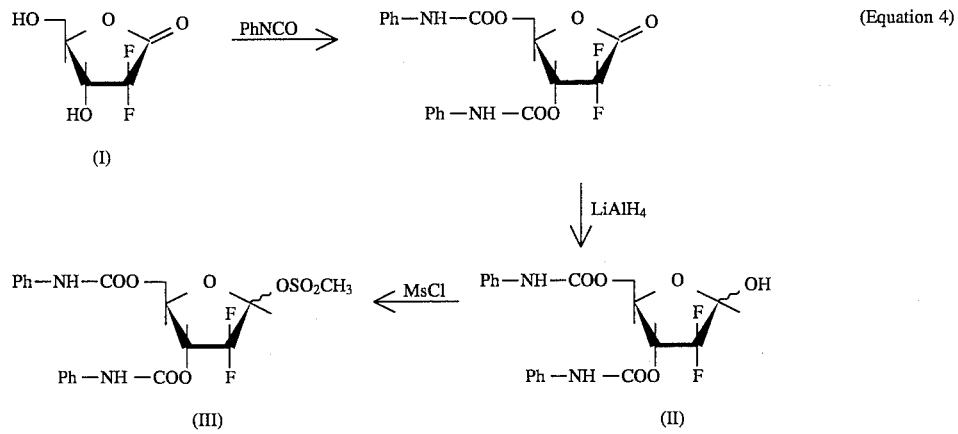

The reaction of the mesylate (III) with silylated cytosine and TMS triflate favored beta isomer synthesis of nucleoside (VIIA; Table 1). After hydrolysis to 2'-deoxy-2',2'-difluoro-beta-cytidine, the beta/alpha ratio (in situ HPLC) was 1.3 (53:47) as compared to where the 3-hydroxy is protected with a benzoyl moiety where the ratio was 0.6 (40:60) (Example 7; Table 1).

The lactone (I) is formed in a known manner by the following conventional reaction (Equation 5):

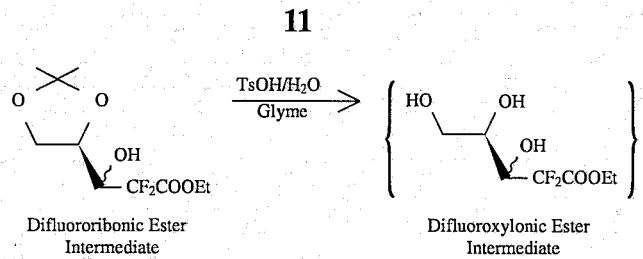

Difluororibonic Ester
Intermediate

Difluoroxylonic Ester
Intermediate

Equation 5

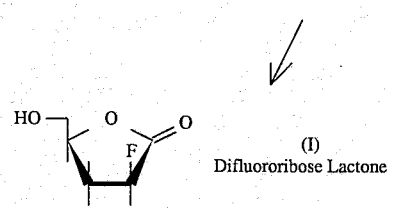

(I)
Difluororibose Lactone

EXAMPLE 2

In order to further explore the effect of carbamoyl substitutions at the 3-position of the deoxyribose intermediates, a route for selectively deprotecting a dibenzoyl mesylate intermediate (IV) at the 3-position was followed to obtain a 5-monobenzoyl mesylate intermediate (V). This intermediate (V) was then reacted with various isocyanates to test the effect of isocyanate substitution to form the C-3 carbamoyl mesylate intermediates (VI). The reaction was as follows (Equation 6)

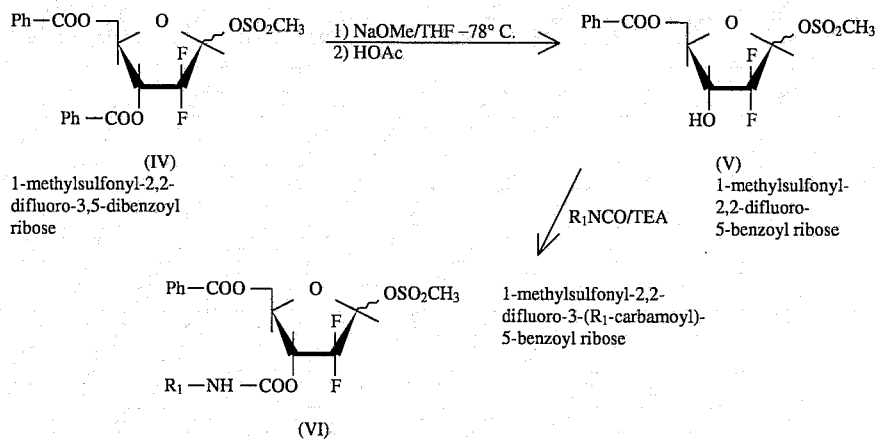

Synthesis of 5-Monobenzoyl Mesylate (V)

To a 100 mL 3-necked round bottom flask (rbf) equipped with a low temperature thermometer and $N_2$ purge was added 2 g dibenzoyl alpha-mesylate (IV) (4.4 mmol) and 80 mL THF. Using magnetic stirring, the contents were cooled to −70° C. to −65° C. with dry ice/acetone bath and 2 mL 25% NaOMe (8.7 mmol) were added. Some solids precipitated, causing the stirrer to stop, but after about 5 minutes agitation resumed. The reaction was followed by HPLC (one drop aliquots added to HPLC vial containing 2 μL HOAc and qs with acetonitrile/$H_2O$). After 45 minutes reaction was virtually complete. After 1 hour stirring 1 mL HOAc (17.5 mmol) was added to quench reaction and flask was allowed to warm to room temperature. Contents containing insoluble salts was mixed in a 500 mL separatory funnel with 200 mL EtOAc and the mixture was extracted twice with 100 mL 20% aqueous NaCl. The solvent phase containing the 5-monobenzoyl mesylate was then dried with anhydrous MgSO$_4$ at room temperature. After filtering to remove the MgSO$_4$ and washing the cake with about 20 mL EtOAc the solvent was concentrated on a rotary vacuum evaporator to a final volume of 40 mL-approximate concentration 0.11 mmol per mL. By HPLC, approximately an equal concentration of methyl benzoate was present as a byproduct with (V).

EXAMPLE 3

Synthesis of 5-Monobenzoyl Mesylate

To a 1 liter 3-necked rbf equipped with a low temperature thermometer, top agitator, and $N_2$ purge was added 20 g dibenzoyl alpha-mesylate (IV) (44 mmol) and 800 mL THF. With vigorous stirring, the contents were cooled to −70° C. with dry ice/acetone bath and 20 mL 25% NaOMe (87.5 mmol) were added with a dropping funnel over about 15 minutes. After 15 minutes additional stirring 10 mL HOAc (175 mmol) were added to quench reaction and flask was allowed to warm to room temperature. Insoluble NaOAc was removed by vacuum filtration with filter aid and the cake was washed with 100 mL THF. The filtrate was concentrated in a rotary vacuum evaporator to an oily residue (30 g) The residue was dissolved in 30 mL EtOAc and 400 mL hexanes were added to precipitate the product as an oil. The methyl benzoate reaction byproduct was mostly with the supernatant. The oily product was extracted twice with 30 mL hexanes, then evaporated in a rotary vacuum evaporator to a final weight of 17 g. By HPLC the methyl benzoate level had been reduced to 6% relative to the 5-monobenzoyl mesylate (VI).

EXAMPLE 4

Synthesis of Alpha 3-Phenylcerbamoyl, 5-Benzoyl Mesylate (VIA; $R_1$ is phenyl)

To a 100 mL 3-necked round bottomed flask (rbf) with condenser, $N_2$ sweep, and magnetic stir bar was added 75 mL solution containing ~2 mmol Compound V, 0.7 mL triethylamine (5 mmol), and 0.6 mL phenyl isocyanate (5.5 mmol). After stirring overnight at room temperature $^{19}$F-NMR indicated reaction was approximately 50% complete. An additional 0.6 mL phenyl isocyanate (5.5 mmol) was added and stirring continued at room temperature for a second night. Reaction was now ~90% complete based on $^{19}$F-NMR An additional 0.3 mL phenyl isocyanate (2.8 mmol) was added and the mixture was stirred at 35° C. for an additional 3 hours. The reaction was now ~96% complete. A precipitate which had formed during the reaction was filtered. This solid contained no fluorine and the $^1$H-NMR spectra was consistent with the expected byproduct diphenyl urea. The filtrate containing the product (VIA) was concentrated, and additional precipitate which formed was removed by filtration. Finally the filtrate was dried in the rotary evaporator to a sticky residue. This was triturated with 25 mL hexanes then air dried to give 1.32 g residue. The residue was mixed with 10 mL toluene at room temperature. Solids not in solution were removed by decantation and filtration. The UV HPLC purity of the product (VIA) in the toluene solution was 85%. The volume of the toluene solution was reduced to about 1 mL and 5 mL hexanes were added and after warming the supernatant was decanted. The air-dried residue (0.5 g) had a UV HPLC purity of 84%. $^{19}$F-NMR indicated that mainly one fluorine containing product was present and the $^1$H-NMR spectra was consistent with the desired product (VIA).

EXAMPLE 5

Synthesis of Alpha 3-(p-Methoxyphenylcarbamoyl)-5-Benzoyl Mesylate (VIB; $R_1$ is p-methoxyphenyl)

To a 10 mL rbf with $N_2$ sweep, and magnetic stir bar was added 2 mL solution containing ~0.22 mmol alpha 5-monobenzoyl mesylate (V) in EtOAc (~0.22 mmol methyl benzoate present as well), 30 µL triethylamine (0.22 mmol), and 57 µL p-methoxyphenyl isocyanate (0.44 mmol). After stirring ~10 minutes at room temperature a precipitate of di(p-methoxyphenyl) urea formed. Reaction was left overnight at room temperature. HPLC and $^{19}$F-NMR indicated reaction was about 50% complete. An additional 57 µL p-methoxyphenyl isocyanate (0.44 mmol) was added and stirring continued at room temperature for 1 hour. The reaction was now >90% complete based on 19F-NMR. The precipitate which had formed during the reaction was vacuum filtered on Whatman 1 paper. The filtrate containing the product (VIB) was concentrated with a stream of air to give 0.17 g of orange gummy residue. A 0.12 g aliquot was triturated with 0.2 mL MTBE to give a white crystal slurry. Decantation left a residue of only 0.01 g. HPLC indicated the supernatant contained significant product so the volume was reduced to ~0.5 mL and 2–2.5 mL hexanes were added to precipitate 0.06 g of an orange "oil" which by HPLC had a UV purity of ~86%. $^{19}$F-NMR indicated that mainly one fluorine containing product was present and the $^1$H-NMR spectra was consistent with the desired product (VIB).

Example 6

Synthesis Of Alpha 3-Carbamoyl-5-Benzoyl Mesylate (VIC; $R_{-1}$ is hydrogen)

To a 10 mL vial with a magnetic stir bar was added 2 mL solution containing ~0.22 mmol alpha 5-monobenzoyl mesylate (II) in EtOAc (~0.22 mmol methyl benzoate present as well), and 0.10 mL chlorosulfonyl isocyanate (1.15 mmol). After stirring ~5 minutes at room temperature reaction was >90% complete (presumably to the chlorosulfonyl carbamoyl derivative) by HPLC. Addition of 1 mL 10% aqueous NaCl resulted in some effervescence with ~60% conversion to the 3-carbamoyl derivative. Vigorous stirring with a second 1 mL aliquot of 10% NaCl gave almost quantitative conversion to the 3-carbamoyl product (V). The ethyl acetate phase was washed with aqueous $NaHCO_3$ and was then dried over anhydrous $Na_2SO_4$. HPLC showed only two UV peaks for the product and methyl benzoate. The extract was blown dry to give 0.079 g of a gummy white residue. $^{19}$F-NHR indicated that mainly one fluorine containing product was present and the $^1$H-NMR spectra was consistent with the desired product (VlC).

Comparative Example 7

Glycosylation Reaction of intermediate 3,5-dibenzoyl mesylate (Equation 1)

To a 10 mL rbf with condenser with a $N_2$ sweep, and magnetic stir bar was added 0,038 g cytosine (0.34 mmol), 1.4 mg $NH_4SO_4$ (0.0106 mmol), 0.17 mL 1,1,1,3,3,3-hexamethyldisilizane (0.81 mmol) and 0.33 mL xylenes. With stirring the mixture was heated to reflux (120° C.–130° C.) and after ~10 minutes a clear solution was obtained. The flask was allowed to cool to ~80° C. and then 0.066 mL TMS triflate (0.34 mmol) and a solution of 0.10 g alpha dibenzoyl mesylate (0.22 mmol) in 0.4 mL xylenes was added to the reaction flask. The mixture was stirred at 90° C. After 6 hours the reaction was approximately 50% complete (HPLC) to dibenzoyl nucleoside with percent beta anomer by HPLC 42%. After holding overnight at ~80° C.–100° C. (reaction was about 80% complete, percent beta anomer by HPLC 40%), the reaction was quenched with 2 mL MeOH and the dibenzoyl nucleoside product (Equation 1) was hydrolyzed with 0.5 mL 25% NaOMe at ~25° C. to give 2'-deoxy-2',2'-difluoro-beta-cytidine (VIII). The percent beta 2'-deoxy-2',2'-difluoro-betacytidine by in situ HPLC was 39%.

EXAMPLE 8

Glycosylation Reaction of Intermediate (VIA)

To a 10 mL rbf with condenser $N_2$ sweep, and magnetic stir bar was added 0,038 g cytosine (0.34 mmol), 1.4 mg $NH_4SO_4$ (0.0106 mmol), 0.17 mL 1,1,1,3,3,3-hexamethyldisilizane (0.81 mmol) and 0.33 mL xylenes. With stirring the mixture was heated to reflux (120° C.–130° C.) and after ~10 minutes a clear solution was obtained. The flask was allowed to cool to ~80° C. and then 0,066 mL TMS triflate (0.34 mmol) and a solution of 0,105 g alpha 3-phenylcarbamoyl-5-benzoyl mesylate (VIA) (~0.11 mmol) in 0.4 mL xylenes was added to the reaction flask. The mixture was stirred at 90° C. After 4 hours the reaction was approximately 60% complete (HPLC) to the nucleoside with percent beta anomer by HPLC 60%. After holding overnight at ~80° C. (reaction about 90% complete, percent beta anomer by HPLC 58%), the reaction was quenched with 2 mL MeOH and the nucleoside product (VIIB) was refluxed with 0.5 mL 25% NaOMe for 30 minutes to give 2'-deoxy-2',2'-difluoro-beta-cytidine. The percent 2'-deoxy-2',2'-difluoro-beta-cytidine by in situ HPLC was 53%.

EXAMPLE 9

Glycosylation Reaction of Intermediate (VIB)

To a 10 mL rbf with condenser $N_2$ sweep, and magnetic stir bar was added 0.02 g cytosine (0.18 mmol), 1.0 mg $NH_4SO_4$ (0.0076 mmol), 0.10 mL 1,1,1,3,3,3-hexamethyldisilizane (0.47 mmol) and 0.16 mL xylenes. With stirring the mixture was heated to reflux (120° C.–130° C.) and after ~5 minutes a clear solution was obtained. The flask was allowed to cool to ~80° C. and then 35 µL TMS triflate (0.18 mmol) and a solution of ~0.06 g alpha 3-(p-methoxyphenylcarbamoyl)-5-benzoyl mesylate (VIB) (~0.10 mmol) in 0.3 mL xylenes was added to the reaction flask. mixture was stirred at 90° C. After 2.5 hours the reaction was approximately 46% complete (HPLC) to nucleoside derivative with percent beta anomer by HPLC 63%. After holding overnight at ~60° C. (reaction only about 50% complete, percent beta anomer by HPLC 61%), the reaction was heated to ~90° C. for 4 hours. Reaction was ~71% complete with percent beta anomer at 59%. After quenching with 2 mL MeOH the dibenzoyl nucleoside product (VIIC) was refluxed with 0.5 mL 25% NaOMe for 60 minutes to give 2'-deoxy-2',2'-difluoro-beta-cytidine. The percent 2'-deoxy-2',2'-difluoro-beta-cytidine by in situ HPLC was 57%.

EXAMPLE 10

Glycosylation Reaction of Intermediate (VIC)

To a 10 mL rbf with condenser, $N_2$ sweep, and magnetic stir bar was added 0,034 g cytosine (0.31 mmol), 1.0 mg $NH_4SO_4$ (0.0075 mmol), 0.10 mL 1,1,1,3,3,3-hexamethyldisilizane (0.47 mmol) and 0.2 mL xylenes. With stirring the mixture was heated to reflux (120° C.–130° C.) and after ~30 minutes a clear solution was obtained. The flask was allowed to cool to ~80° C. and then 0.060 mL TMS triflate (0.30 mmol) and a solution of 0,105 g alpha 3-carbamoyl-5-benzoyl mesylate (VIC) (~0.2 mmol) in 0.4 mL xylenes was added to the reaction flask. The mixture was stirred at 90° C. After holding overnight at ~80° C. followed by 100° C. for 5 hours the reaction was quenched with 3 mL MeOH and the nucleoside product (VIIID) was treated with 1 mL 25% NaOMe for 3 hours at ~25° C. to give 2'-deoxy-2',2'-difluoro-beta-cytidine. The percent beta2'-deoxy-2',2'-difluoro-cytidine by in situ HPLC was 59%.

Table 1 summarizes the results of Examples 7 to 10 and shows that 3-carbamoyl intermediates favorably effect the ratio of beta product produced in the synthesis of Examples 1 and 7 to 10. Where the dibenzoyl mesylate control (Example 7 Equation 1) gives only about 40% by weight beta 2'-deoxy-2',2'-difluorocytidine, 3-carbamoyl substitution on the ribose intermediate substantially increases that percent to, in some cases, close to 60% by weight.

TABLE 1

3'-Beta-Directing Carbamoyl Substituents

| Ex. No. | Mesylate Derivative | Mole Ratio Protected Nucleoside Beta:Alpha | Mole Ratio 2'-deoxy-2',2'-difluoro-cytidine Beta:Alpha |
|---|---|---|---|
| 7 | Ph—COO— [structure with O, F, OSO₂CH₃, Ph—COO, F] (IV) (Prior Art) (Equation 1) | 40:60 | 39:61 |
| 1 | Ph—NH—COO— [structure with O, F, OSO₂CH₃, Ph—NH—COO, F] (III) | 53:47 (VIIA) | 51:39 |

TABLE 1-continued

3'-Beta-Directing Carbamoyl Substituents

| Ex. No. | Mesylate Derivative | Mole Ratio Protected Nucleoside Beta:Alpha | Mole Ratio 2'-deoxy-2',2'-difluoro-cytidine Beta:Alpha |
|---|---|---|---|
| 8 | 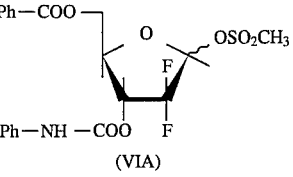 (VIA) | 58:42 (VIIB) | 53:47 |
| 9 | 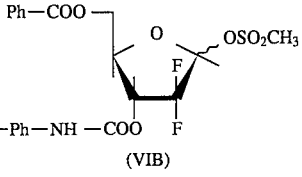 (VIB) | 60:40 (VIIC) | 57:43 |
| 10 | 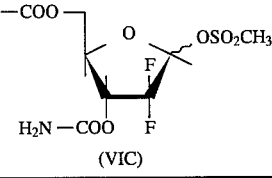 (VIC) | ND (VIID) | 59:41 |

It is intended that the foregoing description be only illustrative of the present invention and that the present invention be limited only by the hereinafter appended claims.

I claim:

1. An intermediate of the formula

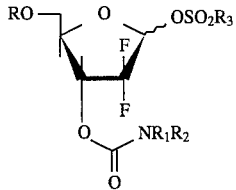

wherein R is a hydroxy protecting group, $R_1$ and $R_2$ are each selected from the group consisting of hydrogen, unsubstituted and substituted $C_1$–$C_8$ alkyl, and unsubstituted and substituted phenyl, and $R_3$ is $C_1$–$C_8$ alkyl.

2. An intermediate of claim 1 wherein $R_1$ and $R_2$ are each selected from the group consisting of hydrogen and phenyl.

3. An intermediate of claim 2 wherein R is phenyl carbamoyl, $R_1$ is hydrogen, and $R_2$ is phenyl.

4. The intermediate of claim 3 wherein $R_3$ is methyl.

5. The intermediate of claim 1 wherein R is benzoyl, $R_1$ is hydrogen, $R_2$ is phenyl, and $R_3$ is methyl.

6. The intermediate of claim 1 wherein R is benzoyl, $R_1$ is hydrogen, $R_2$ is 4-methoxyphenyl, and $R_3$ is methyl.

7. The intermediate of claim 1 wherein R is benzoyl, $R_1$ and $R_2$ are each hydrogen, and $R_3$ is methyl.

8. An intermediate of the formula:

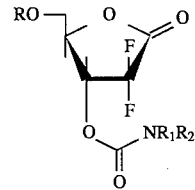

wherein R is a hydroxy protecting group and $R_1$ and $R_2$ are each selected from the group consisting of hydrogen, unsubstituted and substituted $C_1$–$C_8$ alkyl, and unsubstituted and substituted phenyl.

9. An intermediate of claim 8 wherein R is benzoyl or phenylcarbamoyl and $R_1$ and $R_2$ are each selected from the group consisting of hydrogen and phenyl.

10. An intermediate of the formula:

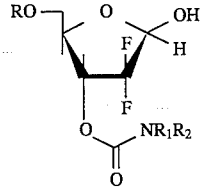

wherein R is a hydroxy protecting group and $R_1$ and $R_2$ are each selected from the group consisting of hydrogen, unsubstituted and substituted $C_1$–$C_8$ alkyl, and unsubstituted and substituted phenyl.

11. An intermediate of claim 10 wherein R is benzoyl or phenylcarbamoyl and $R_1$ and $R_2$ are each selected from the group consisting of hydrogen and phenyl.

12. A process for the preparation of a beta nucleoside of the formula:

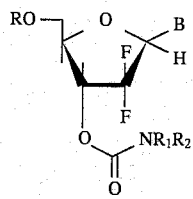

where B is a protected pyrimidine nucleobase residue, which comprises:

reacting an intermediate of the formula:

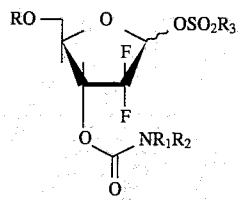

with a protected pyrimidine nucleobase B-H in the presence of a Lewis acid in a non-reactive solvent at a temperature between about 80° and 120° C., wherein R is a hydroxy protecting group, $R_1$ and $R_2$ are each selected from the group consisting of hydrogen, unsubstituted and substituted $C_1$–$C_8$ alkyl, and unsubstituted and substituted phenyl, and $R_3$ is $C_1$–$C_8$ alkyl.

13. The process of claim 12 wherein the nucleobase is a cytosine.

14. The process of claim 12 wherein the catalyst is trimethylsilyltriflate and the solvent is xylene.

15. The process of claim 12 further comprising deprotecting the resulting beta-nucleoside.

16. An intermediate of the formula

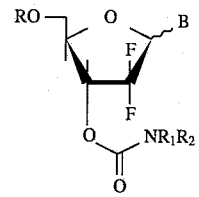

wherein R is a hydroxy protecting group, $R_1$ and $R_2$ are each selected from the group consisting of hydrogen, unsubstituted and substituted $C_1$–$C_8$ alkyl, and unsubstituted and substituted phenyl, and B is selected from the group consisting of a protected and an unprotected pyrimidine nucleobase.

17. An intermediate of claim 16 wherein $R_1$ and $R_2$ are each selected from the group consisting of hydrogen and phenyl.

18. An intermediate of claim 17 wherein R is phenyl carbamoyl, $R_1$ is hydrogen and $R_2$ is phenyl.

19. The intermediate of claim 17 wherein B is trimethylsilyl protected cytosine.

20. The intermediate of claim 16 wherein R is benzoyl, $R_1$ is hydrogen, $R_2$ is phenyl, and B is trimethylsilyl protected cytosine.

21. The intermediate of claim 16 wherein R is benzoyl, $R_1$ is hydrogen, $R_2$ is methoxyphenyl, and B is trimethylsilyl protected cytosine.

* * * * *